United States Patent [19]
Diaz

[11] Patent Number: 5,824,026
[45] Date of Patent: Oct. 20, 1998

[54] CATHETER FOR DELIVERY OF ELECTRIC ENERGY AND A PROCESS FOR MANUFACTURING SAME

[75] Inventor: Cesar M. Diaz, Colorado Springs, Colo.

[73] Assignee: The Spectranetics Corporation, Colorado Springs, Colo.

[21] Appl. No.: 662,799

[22] Filed: Jun. 12, 1996

[51] Int. Cl.$^6$ .................................................. A61N 1/05
[52] U.S. Cl. ........................................ 607/116; 600/373
[58] Field of Search .................................. 128/639, 642; 607/115, 116, 119, 122; 600/372, 373

[56] References Cited

U.S. PATENT DOCUMENTS

| | | | |
|---|---|---|---|
| 4,514,589 | 4/1985 | Aldinger et al. . | |
| 4,559,951 | 12/1985 | Dahl et al. | 607/122 |
| 4,945,342 | 7/1990 | Steinemann . | |
| 4,964,414 | 10/1990 | Handa et al. | 600/373 |
| 5,005,587 | 4/1991 | Scott . | |
| 5,016,646 | 5/1991 | Gotthardt et al. | 607/122 |
| 5,209,229 | 5/1993 | Gilli . | |
| 5,246,014 | 9/1993 | Williams et al. . | |
| 5,303,704 | 4/1994 | Molacek et al. . | |
| 5,324,323 | 6/1994 | Bui | 607/119 |
| 5,324,326 | 6/1994 | Lubin . | |
| 5,330,520 | 7/1994 | Maddison et al. | 607/122 |
| 5,330,521 | 7/1994 | Cohen . | |
| 5,415,653 | 5/1995 | Wardle et al. . | |
| 5,417,208 | 5/1995 | Winkler . | |
| 5,423,881 | 6/1995 | Breyen et al. . | |
| 5,443,492 | 8/1995 | Stokes et al. . | |
| 5,466,252 | 11/1995 | Soukup et al. . | |
| 5,483,022 | 1/1996 | Mar . | |
| 5,569,220 | 10/1996 | Webster, Jr. | 128/639 |
| 5,667,499 | 9/1997 | Welch . | |

FOREIGN PATENT DOCUMENTS

| | | |
|---|---|---|
| 358117 | 3/1990 | European Pat. Off. . |
| 4428914 | 2/1995 | Germany . |
| WO 9416618 | 8/1994 | WIPO . |

*Primary Examiner*—William E. Kamm
*Assistant Examiner*—George R. Evanisko
*Attorney, Agent, or Firm*—Cushman Darby & Cushman IP Group of Pillsbury Madison & Sutro LLP

[57] ABSTRACT

A catheter for delivering electrical energy to a selectable region of a patient's body has at least one layer of fibers with at least one electrically conductive fiber stranded over a flexible core. Each layer of fibers is stranded over the flexible core and underlying layers opposite in direction from that of the immediately preceding layer so as to provide a catheter with good torque transfer properties in addition to its electrical energy transfer properties. The outermost layer of stranded fibers is electrically conductive and is covered by an electrically insulative outer layer which is mechanically strippable to expose selectable regions of the underlying layer of stranded fibers. Electrical energy is transmitted along the outermost layer of stranded fibers to tissue which is in contact with the exposed contact region of the outermost layer of stranded fibers.

22 Claims, 4 Drawing Sheets

CATHETER FOR DELIVERY OF ELECTRIC ENERGY AND A PROCESS FOR MANUFACTURING SAME

BACKGROUND OF THE INVENTION

1. Field of the Invention

The present invention pertains to catheters for delivering electrical energy to internal regions of a patient's body, and more particularly to an electrical energy delivering catheter with stranded electrically conductive wires.

2. Description of Related Art

The term "medical catheter" is a reference to a very large class of known medical devices which share the general feature that they all tend to be tubular in shape and have a sufficiently small diameter such that they may be inserted into the patient's body through either a small incision or a small natural opening. A more specific, yet still somewhat broad, class of catheters has one or more electrodes such that electrical energy may be transferred between the external end of the catheter and internal regions of a patient's body. Such energy transfer can be for either therapeutic or diagnostic functions, or a combination of both. For example, such electrical catheters are known for mapping out the electrical activity of a patient's heart in order to provide data to assist a doctor in making a diagnosis. Electrical catheters are also used as therapeutic instruments to ablate tissue in specific regions of the body, such as heart tissue. Ablative catheters are known which employ a radio frequency electrical power source. Electrical catheters are also known for use in artificially pacing the heart and in defibrillation. The specific number of electrodes employed, the size of the electrodes, and the relative spacing and location of the electrodes on the electrical catheter depend on the particular application.

Many applications require a relatively large surface contact region which serves as the electrical energy transfer electrode. In addition, most applications that require large electrical contact regions also require adequate flexibility such that the catheter can be maneuvered to the desired location, such as a specific region of the heart, and yet be stable and controllable enough to be kept in place.

Prior art devices which simply utilize electrically conductive wires are unsatisfactory as electrodes. The configurations of electrical wires known in the art have smaller contact surfaces than are necessary, and, although such catheters are sufficiently flexible, they are extremely difficult to maintain in good contact with the specific tissue region.

Other prior art devices utilize a thin layer of conductive paint as an electrode. Such devices have the advantages of providing large contact areas and being mechanically flexible. However, they have the disadvantages that the conductive paint tends to chip, peel, and separate from the connecting wire due to the flexing action of the catheter. Therefore, many prior art devices utilize metal rings for the contact region in order to minimize the problems inherent in catheters which use conductive paint. However, catheters with ring electrodes also have problems and limitations. Most fundamentally, the rings are not flexible, thus only small rings are used. These devices also have the problem that one must maintain a good electrical connection between a wire, which typically moves with respect to the ring electrode as the catheter flexes, and the ring electrode. In addition, elaborate production methods are used in order to ensure that the metal ring does not protrude beyond the surrounding surface of the catheter.

Finally, still other prior art devices utilize electrically conductive wires which are braided in a cylindrical mesh which somewhat resembles the pattern of a fishing net. This type of prior art device has several disadvantages. The overlapping wires create spaces which prevent packing the wires closely together. The overlapping wires also create stresses and strains which can lead to wires breaking thus degrading the electrical and mechanical properties of the catheter. In addition, the overlapping wires create gaps which allow the overlying electrically insulative layer to adhere firmly to individual wires. This makes it difficult to mechanically strip away portions of the insulation without damaging the underlying wires.

Another type of catheter, a fiber optic catheter, is known to provide stranded optical fibers thus yielding increased flexure characteristics, an even distribution of bending stresses in the fibers, and a smaller overall diameter for the catheter. (See Wardle et al., U.S. Pat. No. 5,415,653).

It is known in the art that stranding optical fibers such that they define non-overlapping helical paths around a core provides desirable torque transfer properties for rotations of the optical catheter in one direction about its central axis. It is further known that by stranding a plurality of layers of optical fibers such that the direction of stranding is reversed for each successive layer added to the optical catheter provides an optical catheter with good torque transfer properties for rotations in both directions around the central axis of the catheter and good tactile qualities.

SUMMARY OF THE INVENTION

Accordingly, it is an object of this invention to provide a catheter for delivering electrical energy to an internal region of a patient's body through a stable, controllable, and flexible electrical contact region which can be made suitably large.

It is another object of this invention to provide a catheter for delivering electrical energy to an internal region of the patient's body which has no separate electrical connections to the electrical contact region, thus enhancing the reliability of the catheter.

It is another object of this invention to provide a catheter for delivering electrical energy to an internal region of the patient's body through one or more selectable electrical contact regions, such that the size, location, and relative separations of the contact regions are easily and cheaply selectable.

It is a further object of an embodiment of this invention to provide a catheter for electrical energy delivery to an internal region of the patient's body which has at least one electrical conduit of closely or maximally packed electrical wires which closely approximate an electrically conductive cylindrical shell.

It is another object of this invention to provide a catheter for electrical energy delivery to an internal region of the patient's body which has good torque transfer, good maneuverability, and good tactile characteristics.

It is yet another object of this invention to provide a catheter for electrical energy delivery to an internal region of the patient's body which incorporates a plurality of sensors while having good reliability and a good profile.

It is also an object of the present invention to provide a method of manufacturing each embodiment of electrical energy delivering catheters as described in the above objects of this invention.

The above and related objects of the instant invention are realized by stranding electrically conductive fibers over a flexible core. A layer of stranded fibers is comprised of a plurality of fibers which extend substantially between both ends of the catheter along non-overlapping paths, preferably in spiral or helical paths. Since the fibers do not overlap, they can be closely or maximally packed together in a layer which approximates a cylindrical shell conductor. Such a layer of stranded fibers provides a conducting conduit between both ends of the catheter and provides an outer surface to make electrical contact. Thus, the limit for the largest surface contact region for a given catheter, according to an embodiment of this invention, is equal to the entire outer surface of the electrically conductive surface layer. Generally, one will utilize only a fraction of the surface of the stranded layer as an electrical contact region. Therefore, the catheter is typically covered with an outer electrically insulative layer which is mechanically stripped to expose the desired electrical contact regions. The invention has an advantage that the insulative layer is easy to mechanically strip without damaging the underlying layer of stranded fibers.

This yields a flexible catheter for electrical energy delivery which has suitably large electrical contact regions and a low resistance electrical conduit which flows directly into the contact regions without the need for any electrical connections therebetween.

Preferably, the wires are stranded in non-overlapping helical paths around the core with a substantially uniform pitch. In other embodiments of the instant invention, additional stranded and insulative layers are provided between the insulating core and the outer stranded layer to provide certain desirable mechanical and/or electrical properties.

A preferred embodiment of the instant invention also comprises a first layer of stranded fibers over the central core, and a second layer of stranded fibers over the first layer of stranded fibers. The plurality of fibers in each layer of stranded fibers define non-overlapping helical paths with a substantially uniform pitch. Each successive layer of stranded fibers is wound around the underlying structure in a direction opposite to that of the preceding layer of stranded fibers.

In another embodiment of the invention, at least one layer of stranded fibers is made of metal wires which are connected to ground such that they provide a shield for electric fields. Other embodiments of the invention combine alternative combinations of stranded and insulating layers to achieve certain mechanical and electrical structures.

In a preferred embodiment of the invention, the core defines a central lumen which is suitable for accommodating at least one wire or fiber. In other embodiments of the invention, the core defines a plurality of lumens.

In other embodiments of the invention, different types of fibers are mixed with electrically conductive fibers. Optical fibers are included in an embodiment of the invention to carry optical sensor signals or therapeutic energy. In another embodiment of this invention, certain polymer fibers are included to provide enhanced lubricity of the corresponding stranded layer.

The instant invention also encompasses a process for manufacturing an electrical energy delivering catheter by stranding at least one plurality of fibers over a flexible non-conductive core.

DETAILED DESCRIPTION OF THE PREFERRED EMBODIMENTS

Figure 1:
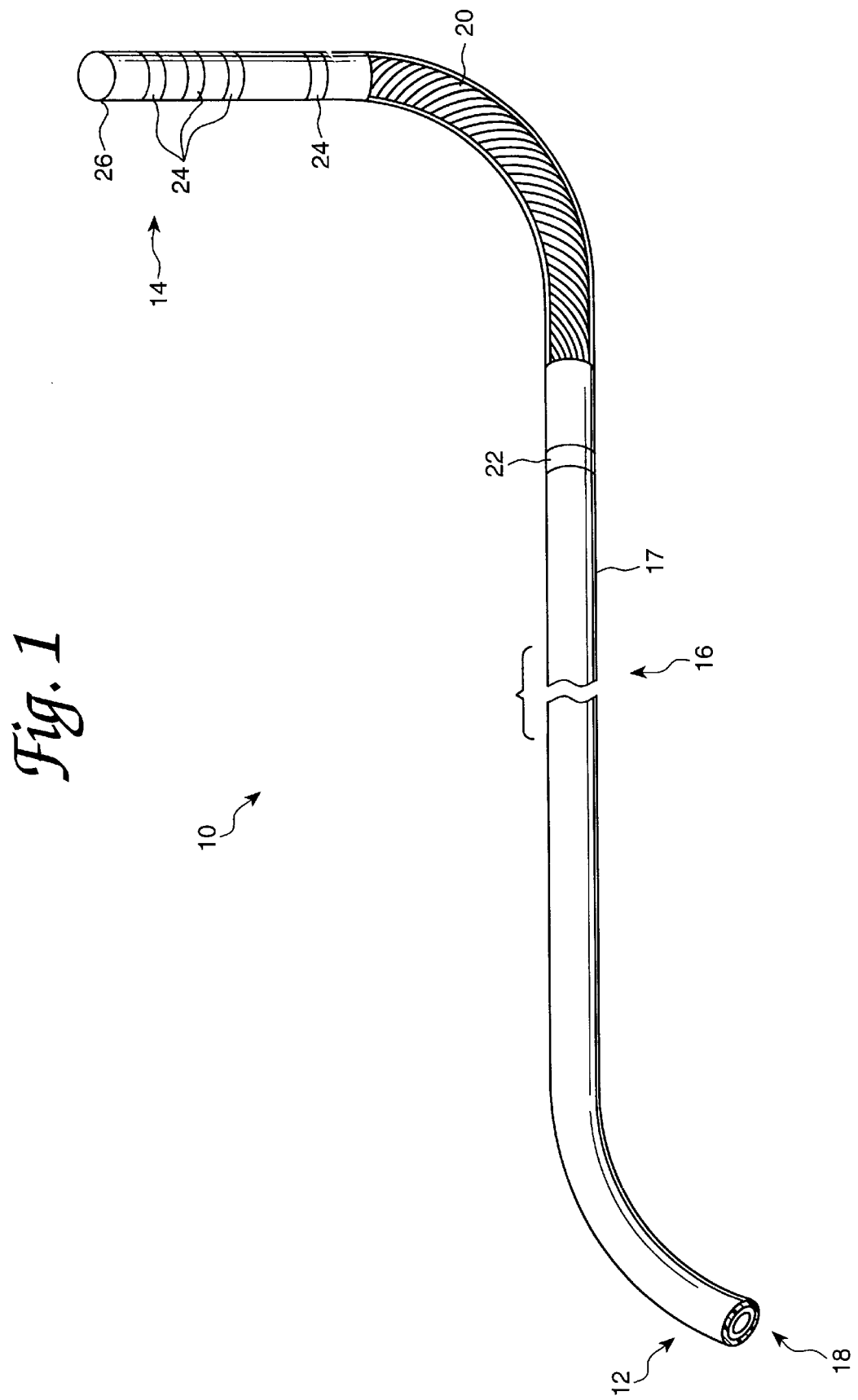
FIG. 1 is a schematic view of a catheter for delivering electrical energy to a region of a patient's body according to the preferred embodiments of the invention.

The catheter of the present invention is designated generally by the reference numeral 10 in FIG. 1. The catheter 10 is depicted with the central section broken away. Consequently, FIG. 1 gives no indication of the length of the catheter 10 relative to its width. The length of the catheter 10 is selectable in accordance with the length of known catheters which are used for the same or similar applications. Generally, the catheter 10 defines a proximal end 12, a distal end 14, and an outer surface 16, with the outer surface being approximately cylindrical in shape within local regions along the length of the catheter 10.

In a preferred embodiment, the outer surface 16 of the catheter 10 is defined by an outer electrically insulating surface layer 17 which fits snugly over an inner composite structure 18. For most uses of this invention, polyurethane is a preferable material for the outer insulating layer 17. However, there are a large number of suitable materials that would be well known to those skilled in the art. For example, polyester ether ketone is a preferable material for the insulating layer 17 in ablative catheters. The outer surface layer 17, in this embodiment, is mechanically strippable at a selectable contact region 20 so as to expose the outer layer of the inner composite structure 18 over the selectable contact region 20. In the example illustrated in FIG. 1, sensors 22 and 24 are attached to selectable locations along the catheter 10, and sensor 26 is attached to the distal end 14.

Figure 2:
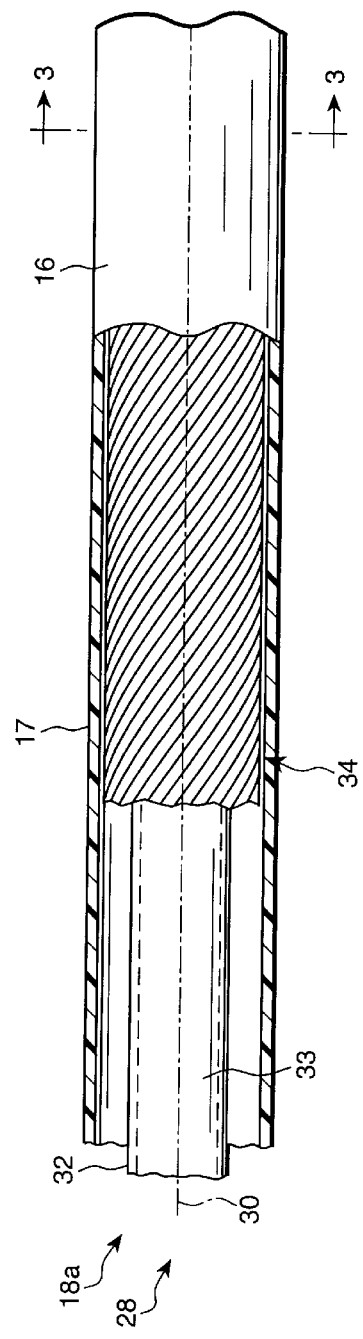
FIG. 2 is a partial cutaway view which shows the inner composite structure of a first embodiment of the invention.
Figure 3:
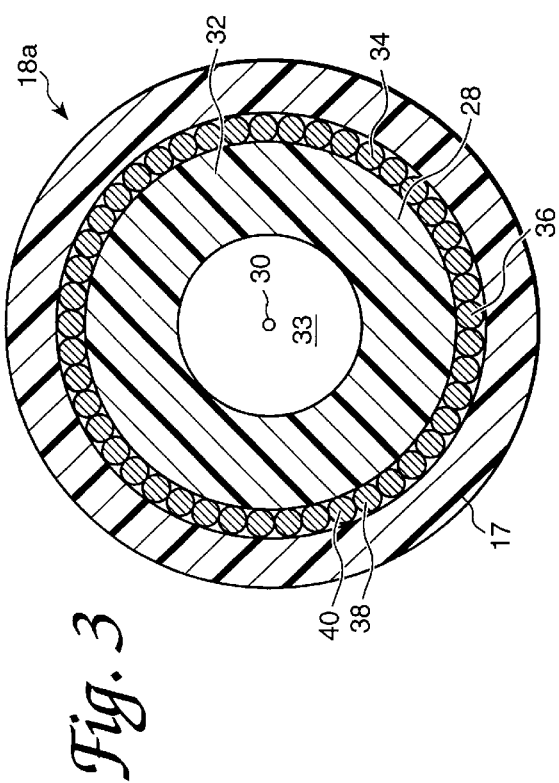
FIG. 3 is a cross-sectional view of the first embodiment taken on section line 3—3 in FIG. 2.

One can best see the inner composite structure 18a of a preferred embodiment in FIGS. 2 and 3. FIG. 2 is a side view of a section of the catheter 10a with partial cutaway sections which reveal the inner composite structure 18a. FIG. 3 provides a cross-sectional view of the catheter 10a. The catheter 10a is generally comprised of a central flexible, electrically non-conductive core 28 disposed along the catheter axis 30. (The term "non-conductive" is used to refer to any material which is generally known to be an insulator, or to a fluid or gas-filled or vacuum space which also acts as an insulator.) In one embodiment of the invention, the core 28 is a solid electrical insulator, and in other embodiments the electrically insulative core 28 defines one or more hollow paths that extend between the proximal end 12 and the distal end 14 of the catheter 10a. In a preferred embodiment, the central non-conductive core 28 is flexible electrically insulative tubing 32 which defines a central lumen 33 that extends along the catheter axis 30. In the preferred embodiment the core is made of polyurethane.

The non-conductive core 28 has a layer of stranded fibers 34 on its outer surface. Stranding optical fibers in a fiberoptic catheter is taught by Wardle et al. in U.S. Pat. No. 5,415,653 entitled "Optical Catheter with Stranded Fibers," and is hereby incorporated by reference in its entirety. The first layer of stranded fibers 34 is comprised of a plurality of fibers, one of which is designated by reference numeral 36 in FIG. 3. Each fiber, such as fiber 36, in the layer of stranded fibers 34 extends substantially between the proximal end 12 and the distal end 14 of the catheter 10a, along non-overlapping, helical paths around the central non-conductive core 28.

The stranded fibers 34 define helical paths with a substantially uniform first pitch angle for all fibers 34 at substantially all points along the helical paths when the catheter 10a subtends a straight line and is in an unstressed, relaxed state.

Generally, each individual fiber, such as fiber 36, has a selectable thickness and composition. For example, fiber 38 may have a different thickness from that of fiber 36, or fiber 38 may be of a different material from that of fiber 36. The layer of stranded fibers 34 is nowhere thicker than the thickness of the thickest fiber. In the example depicted in FIGS. 2 and 3, the fibers 34 are 40±4 electrically conducting wires which are all of approximately equal thickness. The example depicted in FIG. 3 shows individual adjacent fibers, such as fibers 38 and 40, as being contiguous. Other embodiments of this invention include selectable numbers of fibers within the layer of stranded fibers 34, and selectable separations between fibers. The number of fibers are chosen to be greater than 10, preferably 20 or more, and are often chosen in the range of 40, 50, or even greater. In many uses, such as to deliver high voltage defibrillation pulses, the fibers are preferably made from low resistance materials such as platinum, silver or titanium. In this embodiment, the stranded fibers 34 are covered by insulating layer 17 described above.

Figure 4:
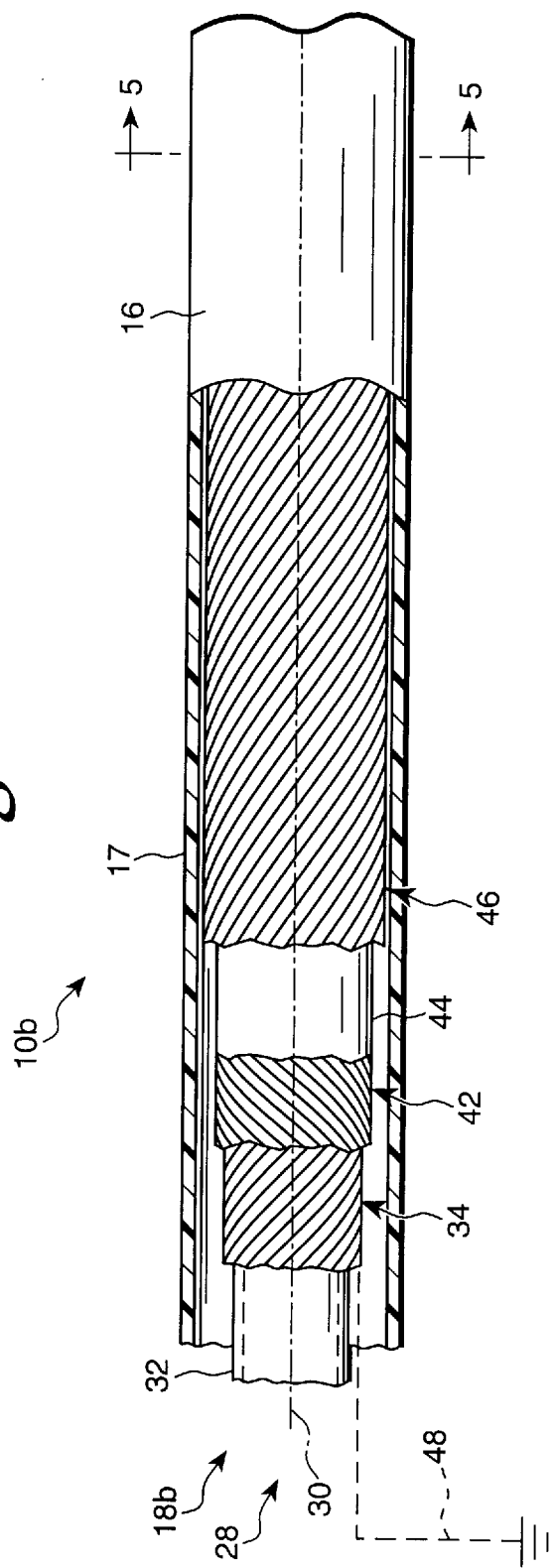
FIG. 4 is a partial cutaway view which shows the inner composite structure of a second embodiment of the invention.
Figure 5:
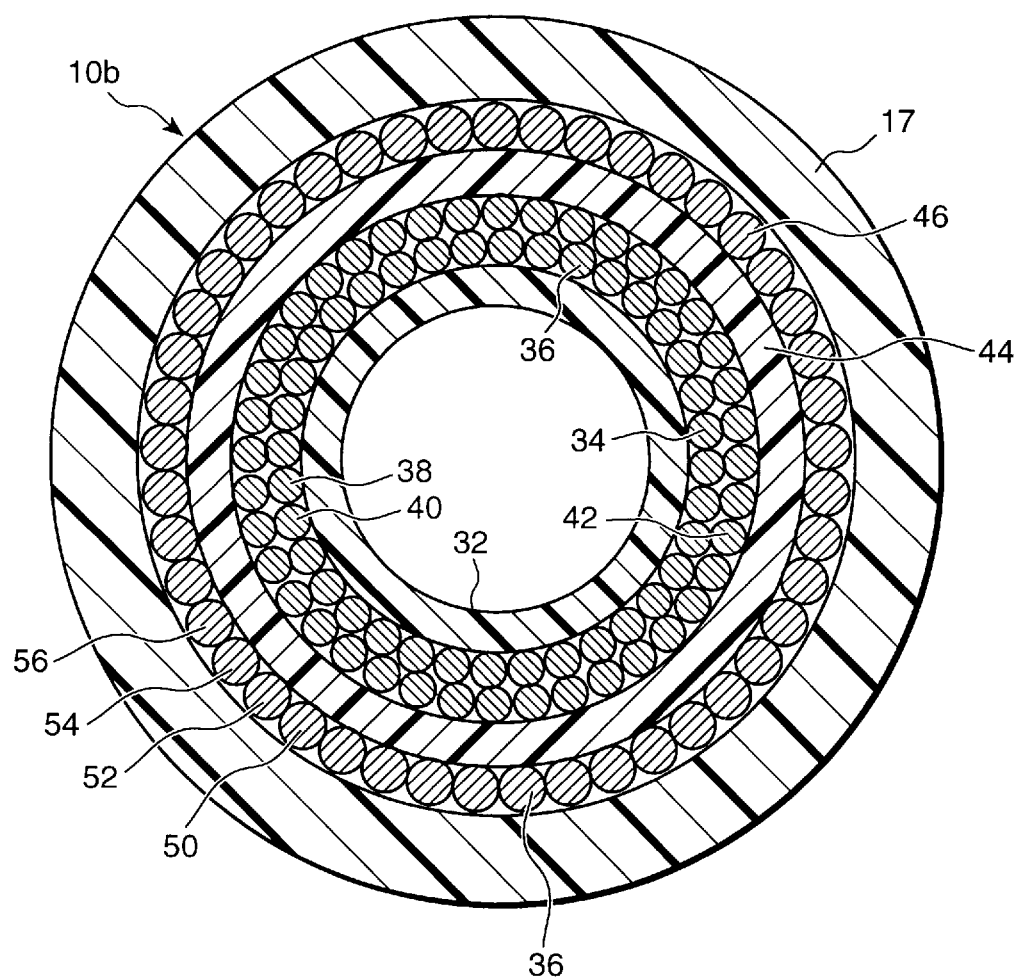
FIG. 5 is a cross-sectional view of the second embodiment of the invention taken on section line 5—5 in FIG. 4.

One can best see the inner composite structure 18b of another preferred embodiment in FIGS. 4 and 5. FIG. 4 is a side view of a section of the catheter 10b with partial cutaway sections which reveal the inner composite structure 18b. FIG. 5 provides a cross-sectional view of the catheter 10b. The catheter 10b is generally comprised of a central flexible, electrically non-conductive core 28 disposed along the catheter axis 30, as described above in reference to the first mentioned preferred embodiment.

This embodiment has a first layer of stranded fibers 34 on the outer surface of the non-conductive core with a second layer of stranded fibers 42 immediately over the first layer of stranded fibers. In this preferred embodiment of the invention, each successive layer of fibers is stranded over the underlying layer in a direction opposite to that of the closest underlying stranded layer. Therefore, according to this preferred embodiment of the invention, the second layer of stranded fibers 42 is stranded over the first layer of stranded fibers 34 in a direction opposite to that of the first layer. The individual fibers of the second layer of stranded fibers 42, and any and all succeeding layers of stranded fibers, are selectable in material and thickness. In a preferred embodiment of the instant invention, there are 38±4 fibers in the first layer and 43±4 fibers in the second layer which are all substantially of equal thickness. The fibers of the first and second layers in this embodiment are preferably of materials with high tensile strength, such as stainless steel. The fibers of the second layer of stranded fibers 42 similarly extend between the proximal end 12 and the distal end 14 of the catheter 10b along non-overlapping helical paths around the first layer of stranded fibers 34. The second layer of stranded fibers 42 is also stranded such that the plurality of fibers define helical paths of a substantially uniform second pitch for all fibers 42 at substantially all points along the helical paths when the catheter 10b subtends a straight line and is in an unstressed, relaxed state. Since the second layer of stranded fibers 42 is stranded around the first layer of stranded fibers 34 in a direction opposite from that of the direction in which the first layer of stranded fibers 34 is stranded around the non-conductive core 28, the second pitch is opposite in sign to that of the first pitch.

Furthermore, the magnitude of the second pitch is approximately equal to the magnitude of the first pitch, which is preferably 0.475 inches. The reader should note that it is known in the art that the pitch of layers of stranded optical fibers can be selectively varied to achieve alternative mechanical properties of a fiberoptic catheter. A greater pitch allows one to strand a greater number of fibers at the expense of some flexibility and torquability. Conversely, a smaller pitch leads to greater flexibility, but a smaller number of fibers in the strand. Similarly, in other embodiments of the instant invention, one can select different and nonuniform first and second pitches in order to obtain desired mechanical properties. Preferably, the pitch is much greater than the thickness of the wire (at least 10 times greater, and more typically more than 40 times greater).

The preferred embodiment depicted by the example of FIGS. 4 and 5 has a first electrically insulative layer 44 immediately covering the second layer of stranded fibers. Polyurethane is a suitable material for layer 44 for most uses, or polyester ether ketone for other uses. A third layer of fibers 46 is stranded over the outer surface defined by the first electrically insulative layer 44. In a preferred embodiment, the third layer of stranded fibers 46 has 40±4 titanium wires, each of which extend substantially between the proximal end 12 and the distal end 14 of the catheter 10b, along non-overlapping helical paths with a third pitch which is substantially equal in magnitude, but opposite in sign to the second pitch. The third layer of stranded fibers 46 is covered by a second layer of electrically insulative material 17 which defines an outer surface 16. When the present embodiment is used as a defibrillation catheter, the second layer of electrically insulative material 17 must be capable of withstanding a DC voltage of 1500 V applied in 20 ms pulses. A layer 17 made of polyurethane with a thickness of at least 0.0035 inches is suitable for catheter 10b with an outer diameter of 0.077±0.002 inches.

In the preferred embodiments of this invention the outermost layer of stranded fibers has a large number of closely or maximally packed electrically conductive fibers. The fibers are arranged so as to approximate an electrically conductive cylindrical shell. The approximation to a cylindrical shell improves as the number of fibers increases. Conversely, small numbers of fibers cannot provide a good approximation to a cylindrical shell, as one can appreciate by considering the extreme cases of only one, two, three or four fibers.

The central lumen of the non-conductive core 28 is adapted to accommodate a plurality of fibers which, in one embodiment, extend between the proximal end 12 and the sensors 22, 24, and 26. More particularly, in a preferred embodiment, the central lumen of the non-conductive core 28 accommodates electrically conductive wires which extend from the proximal end 12 of the catheter 10b to connect to electrodes on the sensor 22, 24, and 26.

The electrodes on sensor 26 are suitable for mapping the electrical activity of the heart by procedures which are well-known to one skilled in the art of modern electrophysiology.

In practice, the catheter 10 is guided through a small incision in the body to the internal regions of interest. The flexible inner core 28, first layer of stranded fibers 34, second layer of stranded fibers 42, first insulating layer 44, third layer of stranded fibers 46, and outer surface layer 17 all act in cooperation to transmit torque between the proximal end 12 and the distal end 14 in a manner known in the art for stranded optical fibers. Depending on the particular application, the electrically conductive fibers of the third (outermost) layer of stranded fibers 46 are electrically connected to a high voltage source, a radio frequency voltage source, signal detection and processing equipment, or other suitable electronic equipment. The contact region 20 provides a suitably large surface area for making electrical contact with the internal region of the body of interest. The contact region 20 is selectable in both size and location along the catheter 10 by stripping away the corresponding material from the electrically insulating surface layer 17. In addition, other embodiments of the instant invention have a plurality of contact regions, similar to contact region 20, which are also selectable in size and location. It is important to point out that, unlike prior art ring electrodes, the contact region 20 does not severely affect the flexibility of the catheter and does not present protruding obstacles. As a specific example, one may connect a high voltage source to the third layer of stranded fibers 46 to deliver defibrillation pulses to a patient's heart through the contact region 20. The outer insulating layer 17 and the first electrically insulative layer 44 ensure that the third layer of stranded fibers 46 is electrically isolated everywhere except at the proximal end 12 of the catheter 10, and at the contact region 20.

In a preferred embodiment of the instant invention, the first layer of stranded fibers 34 and the second layer of stranded fibers 42 are electrically isolated from the central lumen by the electrically insulating core 28, and from the third layer of stranded fibers 46 by the first insulative layer 44. In this embodiment, the first layer of stranded fibers 34 and the second layer of stranded fibers 42 have no electrical connections and thus provide primarily mechanical torque transfer properties. In another preferred embodiment, the first layer of stranded fibers 34 and the second layer of stranded fibers 42 are electrically connected to ground as indicated schematically in FIG. 4 by the reference numeral 48. It can also be readily understood by one of ordinary skill in the art, based upon the teachings of this invention, that the layers 34 and 42 provide a second layer in which electrical energy can be transferred between the proximal end 12 and distal end 14 of the catheter 10, independently of the third layer of stranded fibers 46. Energy transfer along this second channel can be in the form of signals from sensors, for example, or for therapeutic purposes.

In other embodiments of the instant invention, fibers of different materials can be mixed with the electrically conductive fibers. For example, fiber 50 in the third layer of stranded fibers 46, or fiber 40 of the first layer of stranded fibers could be an optical fiber suited for transferring optical signals between the distal end 14 and the proximal end 12 of the catheter 10. A greater number of such optical fibers could be used as necessary. The optical fibers could also be used to deliver therapeutic energy to a tissue site somewhere along the length, or at the distal end 14, of the catheter 10, in addition to the above described electrical energy transfer properties of the catheter 10.

In another embodiment of the instant invention, electrically insulative fibers can be mixed with the electrically conductive fibers. For example, as one may best see in FIG. 5, the fiber labeled with the reference numeral 50 may be an electrically conductive wire. The fiber 52 may be an insulative fiber, fiber 54 conductive, fiber 56 insulative, and so on around the third layer of fibers 46. This embodiment yields a plurality of separate electrically conductive channels, e.g., fiber 50 would be one channel, fiber 54 another channel, and so on. This embodiment of the instant invention is not limited to the one specific example described above. One could choose the numbers of electrically insulative and conductive fibers, and the specific configuration of those fibers, from among all of the possible permutations to suit the particular application.

In another embodiment of the instant invention, one may utilize a plurality of different fiber types in order to select specific mechanical properties, in addition to the electrical properties of the catheter 10, to suit a particular application. For example, a fiber such as fiber 40 in the first layer of stranded fibers 34, and any number of other fibers in any of the stranded layers, can be made from certain polymers so as to enhance the lubricity of the corresponding layer.

The preferred embodiment described in detail above, in which a first layer of fibers 34 is stranded over a central core 28, followed by a second layer of stranded fibers 42, a first layer of insulation 44, a third layer of stranded fibers 46, and finally an outer layer of insulation 17, does not limit the invention to that specific configuration. Other embodiments have various numbers of layers of stranded fibers configured with various numbers of intervening electrically insulative layers. Alternatively, the stranded fibers can be provided with an insulating or lubricious coating.

As noted, there are numerous advantages of the catheter of this invention over other catheters for the delivery of electrical energy. The catheter of this invention provides a relatively large surface contact region for transferring electrical energy to an internal region of the body and it is also flexible at the contact region. There are no electrical connections between the contact regions and the wires that transfer the electrical energy to the contact regions, such as is the case with the prior art ring electrodes, thus, enhancing the reliability of the catheter. There are no complicated manufacturing techniques required to ensure that the contact region does not protrude beyond the diameter of the adjacent regions of the catheter, so as not to obstruct the motion of the catheter through narrow paths within the patient's body. The electrically conductive fibers can be closely packed together, so as to approximate a cylindrical sheet conductor.

A plurality of wires which carry an electrical current to the surface contact region has a lower overall resistance than a single wire of the same material of the same thickness that carries the same amount of current to contact regions. Therefore, the stranded wires allow the current to be spread over a region which approximates a cylindrical shell of current. As one strands wires closer together, one more closely approximates the limit of an electrically conductive cylindrical shell. This is particularly true when the wires are stranded so closely together that they are in contact with the immediately adjacent fibers. In such a case, if the wires do not have insulating outer layers, current can then also flow between wires. This additional degree of freedom for the flow of electrical current leads to an additional decrease in the overall electrical resistance, thus, even more closely approximating a conducting ring while remaining flexible.

Therefore, this invention minimizes undesirable resistive heating effects while still providing a central lumen for other instruments and sensors, all while maintaining a compact, narrow cross-section.

Although the invention has been described with reference to specific embodiments, one should realize that these embodiments are illustrative of the application of the principles of the invention. One should recognize from the above description that there are a very large number of modifications and rearrangements of the above-illustrated embodiments which one may devise without departing from the spirit and scope of the invention.

What is claimed is:

1. A catheter comprising:

a core having an axis extending between a proximal end and a distal end of said catheter;

a first layer of stranded fibers stranded over said core;

a first electrically non-conductive layer disposed over said layer of stranded fibers such that said first layer of stranded fibers is enclosed substantially within an interior space defined by said first electrically non-conductive layer, a second layer of stranded fibers stranded over said core;

said second layer of stranded fibers being disposed between said first layer of stranded fibers and said core;

a second electrically non-conductive layer, said second electrically non-conductive layer being disposed between said first layer of stranded fibers and said second layer of stranded fibers thereby preventing flow of electrical current between said first layer and said second layer of stranded fibers; and a third layer of stranded fibers stranded over said second layer of stranded fibers, wherein said third layer of stranded fibers is disposed between said first non-conductive layer and said second layer of stranded fibers, said second and third layers of stranded fibers thereby providing structural support for said catheter, said first layer of stranded fibers includes a plurality of electrically conductive fibers stranded between said proximal end and said distal end thus permitting a transfer of electrical energy between said proximal end and said distal end of said catheter along said plurality of electrically conductive fibers, substantially all fibers of said first layer of stranded fibers are arranged to form a substantially contiguous layer of stranded fibers, and said core, said first layer of stranded fibers, and said first electrically non-conductive layer act in cooperation to provide structural support to said catheter and to permit a transfer of torque between said proximal end and said distal end of said catheter.

2. A catheter according to claim 1, wherein at least one of said second and third layers of stranded fibers includes at least one electrically conductive fiber thereby providing a path to transmit electrical energy between said proximal end and said distal end of said catheter independently of said first layer of stranded fibers.

3. A catheter according to claim 2, further comprising a grounding lead in electrical contact with said at least one electrically conductive fiber thus providing a shield of electric fields.

4. A catheter according to claim 1, wherein said core is an electrically non-conductive core.

5. A catheter according to claim 1, wherein said core defines at least one lumen between said proximal end and said distal end of said catheter.

6. A catheter according to claim 1, wherein said substantially all fibers of said first layer of stranded fibers extend between said proximal end and said distal end of said catheter along non-overlapping helical paths which define a substantially uniform pitch.

7. A catheter according to claim 1, wherein
said substantially all fibers of said first layer of stranded fibers are all substantially equal in thickness,
said first layer of stranded fibers layer has a maximum thickness equal to a thickness of one of said substantially all fibers, and
a number of fibers in said first layer of stranded fibers is substantially equal to a maximum number of fibers of said maximum thickness that can fit within said layer so as to approximate an electrically conductive cylindrical shell.

8. A catheter according to claim 1, wherein said first electrically non-conductive layer defines an exposed contact region allowing electrical contact to be made with said first layer of stranded fibers.

9. A catheter according to claim 1, wherein a fiber of said first layer of stranded fibers has a coating that makes said fibers lubricous.

10. A catheter according to claim 1, wherein a fiber of said first layer of stranded fibers has an electrically insulative coating that impedes a flow of electricity between said fiber and adjacent fibers.

11. A catheter according to claim 1, wherein said first layer of stranded fibers includes an optical fiber which transmits optical energy between said proximal end and said distal end of said catheter.

12. A catheter according to claim 1, wherein said first layer of stranded fibers includes a polymer monofilament fiber which provides lubricity to said layer.

13. A catheter according to claim 1, wherein said first layer of stranded fibers includes a plurality of electrically insulative fibers, said plurality of electrically conductive fibers being disposed such that they are spaced apart by said plurality of electrically insulative fibers to form a plurality of electrically conductive paths within said layer of stranded fibers.

14. A catheter comprising:

a core having an axis extending between a proximal end and a distal end of said catheter;

a first layer of stranded fibers stranded over said core;

a second layer of fibers stranded over said core, said second layer of fibers being disposed between said first layer of stranded fibers and said core;

an electrically non-conductive layer disposed between said first layer of stranded fibers and said second layer of stranded fibers thereby preventing flow of electrical current between said first and said second layers of stranded fibers; and a third layer of stranded fibers stranded over said second layer of stranded fibers such that said third layer of stranded fibers is disposed between said non-conductive layer and said second layer of stranded fibers, said second and third layers of stranded fibers thereby being suitable to provide structural support for said catheter, wherein said first layer of stranded fibers includes at least one electrically conductive fiber, said fibers being stranded between said proximal end and said distal end thus permitting transfer of electrical energy between said proximal end and said distal end of said catheter along said electrically conductive fiber, said second layer of stranded fibers extends from said proximal end to said distal end along non-overlapping helical paths such that each fiber of said second plurality of fibers has a first pitch at a first perpendicular projection of a point along said axis, said third layer of stranded fibers extends from said proximal end to said distal end along non-overlapping helical paths such that each fiber of said third plurality of fibers has a second pitch at a second perpendicular projection of said point along said axis, wherein said second pitch is substantially equal in magnitude and opposite in sign to said first pitch, said non-conductive layer is disposed immediately proximate to said third layer of stranded fibers, said third layer of stranded fibers is disposed immediately proximate to said second layer of stranded fibers, and said second layer of stranded fibers is disposed immediately proximate to said core, wherein said core, said second and third layers of stranded fibers, and said non-conductive layer act in cooperation to transmit torque along said axis of said catheter for rotations in both directions about said axis.

15. A catheter according to claim 14, wherein substantially all fibers of said first layer of fibers are electrical conductors such that said first layer is substantially an electrically conductive layer suitable to transmit electrical energy along said axis of said catheter.

16. A catheter according to claim 15, wherein said core defines a hollow path extending between said proximal end and said distal end such that said hollow path can accommodate at least one wire threaded therethrough.

17. A catheter according to claim 15, wherein said core defines a plurality of hollow paths extending between said proximal end and said distal end.

18. A catheter according to claim 14, further comprising a second electrically non-conductive layer disposed immediately proximate to said first layer of stranded fibers such that said first layer of stranded fibers is enclosed substantially within said second non-conductive layer, said second non-conductive layer thereby preventing flow of electrical current between said first layer of stranded fibers and a body in contact with an outer surface of said second non-conductive layer.

19. A catheter according to claim 18, wherein said second non-conductive layer defines an exposed contact region allowing electrical contact to be made with said first layer of stranded fibers.

20. A catheter according to claim 19, wherein said core defines a hollow path extending between said proximal end and said distal end such that said hollow path can accommodate at least one wire threaded therethrough.

21. A catheter according to claim 20, wherein substantially all of said first layer of fibers are electrical conductors such that said contact region is suitable to transmit electrical energy between said catheter and a body in contact with said contact region.

22. A catheter according to claim 19, wherein said core defines a plurality of hollow paths extending between said proximal end and said distal end.

* * * * *